(12) United States Patent
Gupta et al.

(10) Patent No.: US 12,103,913 B2
(45) Date of Patent: Oct. 1, 2024

(54) SPIROBIINDANE DERIVATIVES AND A PROCESS FOR PREPARATION THEREOF

(71) Applicant: Reliance Industries Limited, Mumbai (IN)

(72) Inventors: Virendrakumar Gupta, Navi Mumbai (IN); Parthiv Mukundkumar Trivedi, Dombivali (IN)

(73) Assignee: Reliance Industries Limited, Mumbai (IN)

( * ) Notice: Subject to any disclaimer, the term of this patent is extended or adjusted under 35 U.S.C. 154(b) by 822 days.

(21) Appl. No.: 17/257,941

(22) PCT Filed: Jul. 3, 2019

(86) PCT No.: PCT/IB2019/055657
§ 371 (c)(1),
(2) Date: Jan. 5, 2021

(87) PCT Pub. No.: WO2020/008375
PCT Pub. Date: Jan. 9, 2020

(65) Prior Publication Data
US 2021/0284595 A1  Sep. 16, 2021

(30) Foreign Application Priority Data

Jul. 5, 2018 (IN) .............................. 201821025187

(51) Int. Cl.
| C07C 68/08 | (2006.01) |
| C07C 67/317 | (2006.01) |
| C07C 68/02 | (2006.01) |
| C07C 69/94 | (2006.01) |
| C07C 69/96 | (2006.01) |

(52) U.S. Cl.
CPC ............ C07C 68/08 (2013.01); C07C 67/317 (2013.01); C07C 68/02 (2013.01); C07C 69/94 (2013.01); C07C 69/96 (2013.01)

(58) Field of Classification Search
CPC ....... C07C 68/08; C07C 67/317; C07C 68/02; C07C 69/96; C07C 69/94
See application file for complete search history.

(56) References Cited

U.S. PATENT DOCUMENTS

| 3,658,941 | A | 4/1972 | Pulkkinen |
| 4,385,111 | A | 5/1983 | Nakamura et al. |
| 4,952,470 | A | 8/1990 | Tamaki et al. |
| 7,838,694 | B2 * | 11/2010 | Naidu .................. C07D 305/14 549/511 |

FOREIGN PATENT DOCUMENTS

EP 2256797 A2 12/2010

OTHER PUBLICATIONS

PubChem CID 66162, National Center for Biotechnology Information. PubChem Compound Summary for CID 66162, 1,1'-Spirobi[1H-indene]-5,5',6,6'-tetrol, 2,2',3,3'-tetrahydro-3,3,3',3'-tetramethyl-. https://pubchem.ncbi.nlm.nih.gov/compound/66162. Accessed Sep. 5, 2023, Mar. 26, 2005. (Year: 2005).*
Ogura et al., Journal of Polymer Science, Part A: Polymer Chemistry (2007), 45(4), 661-668. (Year: 2007).*
Wang Y et al., "A spiro-centered thermopolymerizable fluorinated macromonomer: synthesis and conversion to the high performance polymer," RSC Advances, The Royal Society of chemistry, DOI: 10.1039/c7ra01146F, vol. 7, pp. 18861-18866, dated Mar. 28, 2017 (6 pages).
International Search Report issued in International Application No. PCT/IB2019/055657 dated Aug. 23, 2019 (3 pages).
Written Opinion issued in International Application No. PCT/IB2019/055657 dated Aug. 23, 2019 (4 pages).

* cited by examiner

*Primary Examiner* — Laura L Stockton
(74) *Attorney, Agent, or Firm* — Osha Bergman Watanabe & Burton LLP

(57) ABSTRACT

The present disclosure relates to spirobiindane derivatives and a process for preparation of the same. Spirobiindane derivatives are used as intermediates for many commercially important compounds such as chiral polymers. The present disclosure provides a simple and economical process for the preparation of spirobiindane derivatives of Formula (I) with high yield and having high purity.

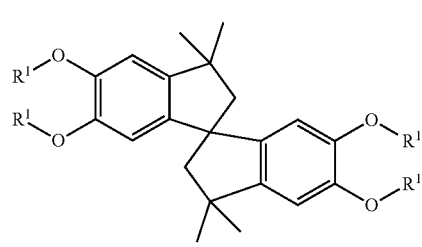

7 Claims, 6 Drawing Sheets

SPIROBIINDANE DERIVATIVES AND A PROCESS FOR PREPARATION THEREOF

FIELD

The present disclosure relates to spirobiindane derivatives and a process for preparation thereof.

Definition

As used in the present disclosure, the following term is generally intended to have the meaning as set forth below, except to the extent that the context in which it is used indicate otherwise.

Protecting Agent: in the context of the present disclosure, a protecting agent relates to a chemical compound capable of introducing a protecting group into a molecule by chemical modification of a functional group present in the molecule.

BACKGROUND

Spirobiindane derivatives have found substantial utility as, among other things, precursors for polymer synthesis. Conventional processes for the preparation of spirobiindane derivatives are associated with drawbacks such as complex reaction procedures and formation of by-products, thereby making the process un-economical. Further, these conventional processes provide the product with low yield and low purity.

The purity of spirobiindane derivatives directly affects the quality of the synthesized compounds. Thus, it is important to synthesize spirobiindane derivatives with a high purity.

There is, therefore, felt a need to provide a simple and economical process for the preparation of spirobiindane derivatives, which mitigates the drawbacks hereinabove.

OBJECTS

Some of the objects of the present disclosure, which at least one embodiment herein satisfies, are as follows:

An object of the present disclosure is to ameliorate one or more problems of the prior art or to at least provide a useful alternative.

Another object of the present disclosure is to provide spirobiindane derivatives.

Yet another object of the present disclosure is to provide a process for the preparation of spirobiindane derivatives with high yield and high purity.

Still another object of the present disclosure is to provide a simple and economical process for the preparation of spirobiindane derivatives.

Other objects and advantages of the present disclosure will be more apparent from the following description, which is not intended to limit the scope of the present disclosure.

SUMMARY

The present disclosure relates to spirobiindane derivatives and a process for the preparation of the same.

In one aspect, the present disclosure provides spirobiindane derivatives of Formula I

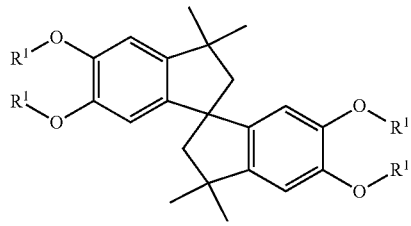

wherein, $R^1$ is selected from the group consisting of hydrogen, alkyl, aryl, heterocyclic, acyl, and benzoyl.

Typically, the spirobiindane derivative is selected 3,3,3',3'-tetramethyl-2,2',3,3'-tetrahydro-1,1'-spirobiindane-5,5',6,6'-tetrayl tetrabenzoate (Ia) and tetraethyl 3,3,3',3'-tetramethyl-2,2',3,3'-tetrahydro-1,1'-spirobiindane-5,5',6,6'-tetracarbonate (Ib) and is represented as

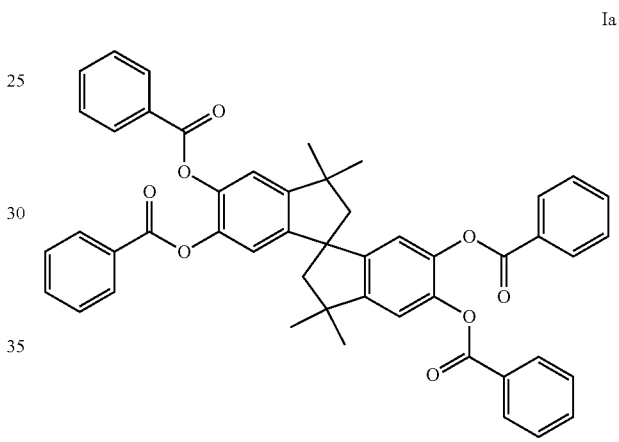

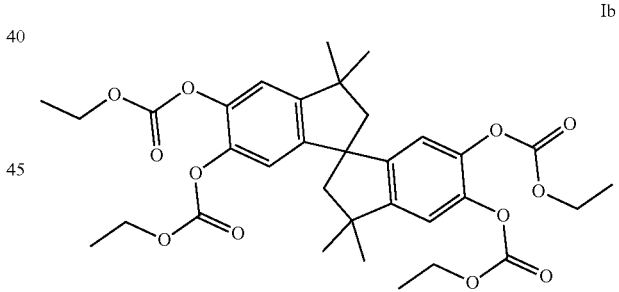

In another aspect, the present disclosure provides a process for the preparation of spirobiindane derivatives of Formula I

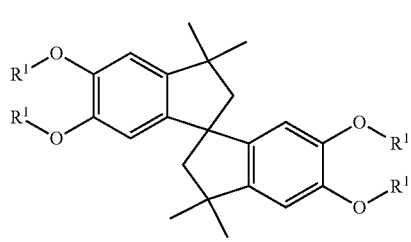

The process comprises reacting 3,3,3',3'-tetramethyl-2,2',3,3'-tetrahydro-1,1'-spirobiindane-5,5',6,6'-tetraol, which is represented as Formula II

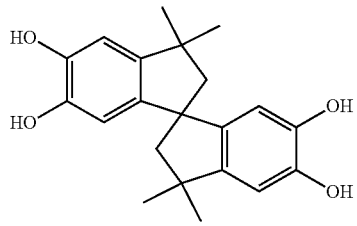

II with a protecting agent and pyridine as a base in a first fluid medium at a predetermined temperature for predetermined time period to obtain a resultant comprising a crude spirobiindane derivative and unreacted pyridine. The unreacted pyridine is separated from the resultant to obtain a crude spirobiindane derivative. The crude spirobiindane derivative is further purified by crystallization using at least one second fluid medium to obtain crystals of spirobiindane derivative of Formula I having purity greater than 95%.

BRIEF DESCRIPTION OF THE ACCOMPANYING DRAWING

The present disclosure will now be described with the help of the accompanying drawing, in which.

DETAILED DESCRIPTION

Figure 1A:
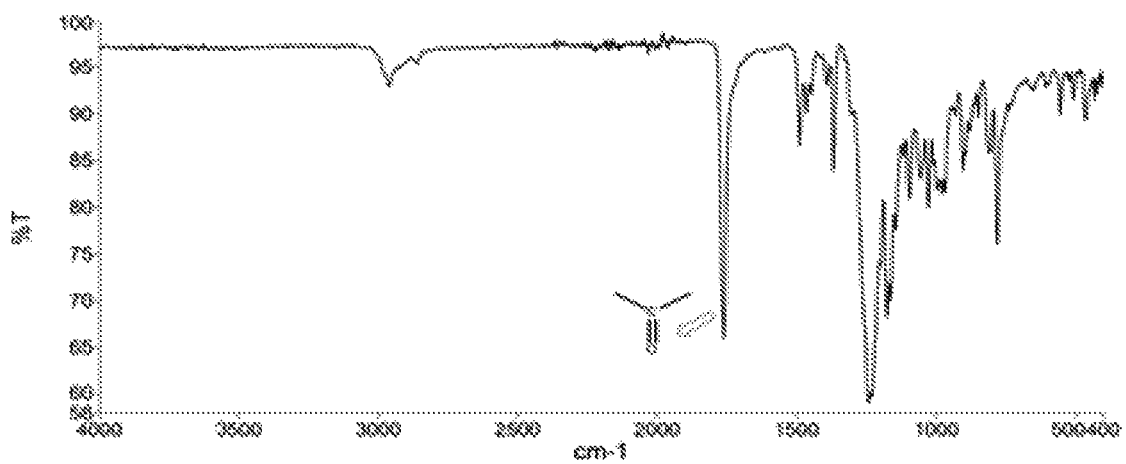
FIG. 1(a) illustrates FTIR (Fourier Transform Infrared) analysis of tetraethyl 3,3,3',3'-tetramethyl-2,2',3,3'-tetrahydro-1,1'-spirobiindane-5,5',6,6'-tetracarbonate.

Spiribiindane derivatives are important building blocks for the synthesis of polymers. The present disclosure envisages a simple and an economical process for the preparation of spirobiindane derivatives with high yield and having high purity.

In one aspect, the present disclosure provides spirobiindane derivatives of Formula I

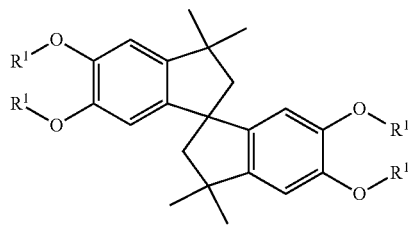

I wherein, $R^1$ is selected from the group consisting of hydrogen, alkyl, aryl, heterocyclic, acyl, and benzoyl.

In accordance with the embodiments of the present disclosure, the spirobiindane derivative is selected from 3,3,3',3'-tetramethyl-2,2',3,3'-tetrahydro-1,1'-spirobiindane-5,5',6,6'-tetrayl tetrabenzoate (Ia) and tetraethyl 3,3,3',3'-tetramethyl-2,2',3,3'-tetrahydro-1,1'-spirobiindane-5,5',6,6'-tetracarbonate (Ib) and is represented as

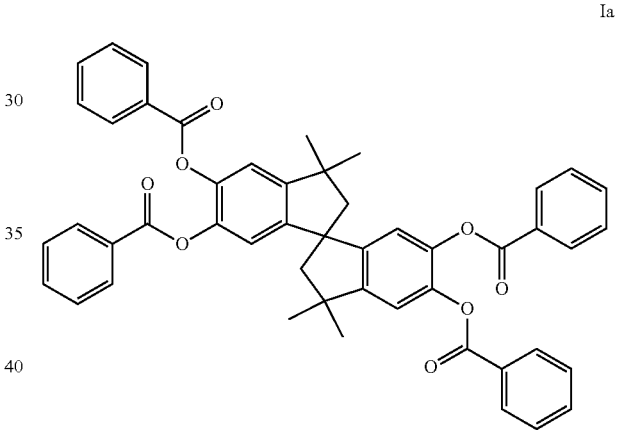

Ia

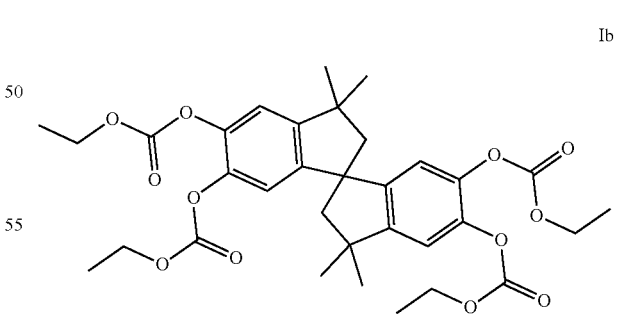

Ib

In another aspect, the present disclosure provides a process for the preparation of spirobiindane derivative of a Formula I. The process is disclosed in detail herein below.

Initially, the reactor is charged with at least one first fluid medium, pyridine and 3,3,3',3'-tetramethyl-2,2',3,3'-tetrahydro-1,1'-spirobiindane-5,5',6,6'-tetraol, which is represented as Formula II.

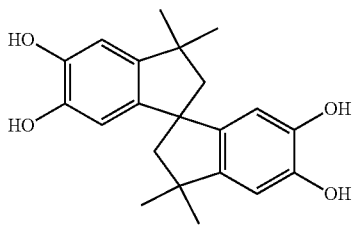

II

A protecting agent is added to the reactor and the mixture is stirred at a predetermined temperature for predetermined time period to obtain a resultant comprising a crude spirobiindane derivative and unreacted pyridine.

The unreacted pyridine is separated from the resultant to obtain a crude spirobiindane derivative.

The crude spirobiindane derivative is further purified by crystallization using at least one second fluid medium to obtain crystals of spirobiindane derivative of Formula I.

In accordance with the process of the present disclosure, the step of separating the unreacted pyridine from the resultant further comprises adding at least one third fluid medium and water to the resultant to obtain a biphasic mixture comprising an aqueous layer and an organic layer. The organic layer is separated from the biphasic mixture. The so obtained organic layer is washed and dried to obtain a crude spirobiindane derivative.

The protecting agent is at least one selected from the group consisting of chloromethyl ether, allyl chloride, t-butyl dimethylsilyl chloride, t-butyl diphenyl silyl chloride, acetyl chloride, pivaloyl chloride, ethyl chloroformate and benzoyl chloride.

In accordance with one exemplary embodiment of the present disclosure, the protecting agent is benzoyl chloride.

In accordance with another exemplary embodiment of the present disclosure, the protecting agent is ethyl chloroformate.

The mole ratio of the compound of Formula II and the protecting agent is in the range of 1:4 to 1:10.

The mole ratio of the compound of Formula II and pyridine is in the range of 1:5 to 1:15.

The first fluid medium is at least one selected from the group consisting of tetrahydrofuran, dioxane, and toluene. In accordance with an exemplary embodiment of the present disclosure, the first fluid medium is tetrahydrofuran.

The second fluid medium and the third fluid medium are independently selected from the group consisting of toluene, n-hexane, pet ether, and diethyl ether.

The predetermined temperature can be in the range of 0° C. to 120° C.

In accordance with one exemplary embodiment of the present disclosure, the predetermined temperature is in the range of 20° C. to 40° C.

In accordance with another exemplary embodiment of the present disclosure, the predetermined temperature is in the range of 100° C. to 110° C.

The predetermined time period is in the range of 2 hours to 6 hours.

The process of the present disclosure is simple and employs inexpensive and readily available reagents. Thus, the process of the present disclosure is economical. The spirobiindane derivative obtained by the process of the present disclosure has purity greater than 95% and yield greater than 80%.

The present disclosure is further described in light of the following laboratory experiments which are set forth for illustration purpose only and not to be construed for limiting the scope of the disclosure. The following laboratory scale examples can be scaled up to industrial/commercial scale.

EXPERIMENTAL DETAILS

Experiment 1: Preparation of tetraethyl 3,3,3',3'-tetramethyl-2,2',3,3'-tetrahydro-1,1'-spirobiindane-5,5',6,6'-tetracarbonate Initially, the reactor was charged with 3,3,3',3'-tetramethyl-2,2',3,3'-tetrahydro-1,1'-spirobiindane-5,5',6,6'-tetraol (5 g), pyridine (11.9 mL) and anhydrous tetrahydrofuran (80 mL). Ethyl chloroformate (11.2 mL) was then added to the reactor and the mixture was stirred at 30° C. was for 4 hours to obtain a resultant comprising tetraethyl 3,3,3',3'-tetramethyl-2,2',3,3'-tetrahydro-1,1'-spirobiindane-5,5',6,6'-tetracarbonate and the unreacted pyridine.

The reaction was monitored by thin layer chromatography. After completion of reaction, water and diethyl ether were added to the resultant to obtain a biphasic mixture comprising an aqueous layer and an organic layer. The organic layer was separated from the biphasic mixture, followed by washing and drying under reduced pressure to obtain crude tetraethyl 3,3,3',3'-tetramethyl-2,2',3,3'-tetrahydro-1,1'-spirobiindane-5,5',6,6'-tetracarbonate.

Crude tetraethyl 3,3,3',3'-tetramethyl-2,2',3,3'-tetrahydro-1,1'-spirobiindane-5,5',6,6'-tetracarbonate was by crystallization using a mixture of diethyl ether and n-hexane.

The purity of tetraethyl 3,3,3',3'-tetramethyl-2,2',3,3'-tetrahydro-1,1'-spirobiindane-5,5',6,6'-tetracarbonate was analyzed by HPLC and was found to be more than 98.4% and the yield was 84%.

The Melting point was 128° C.-130° C.

Figure 1B:
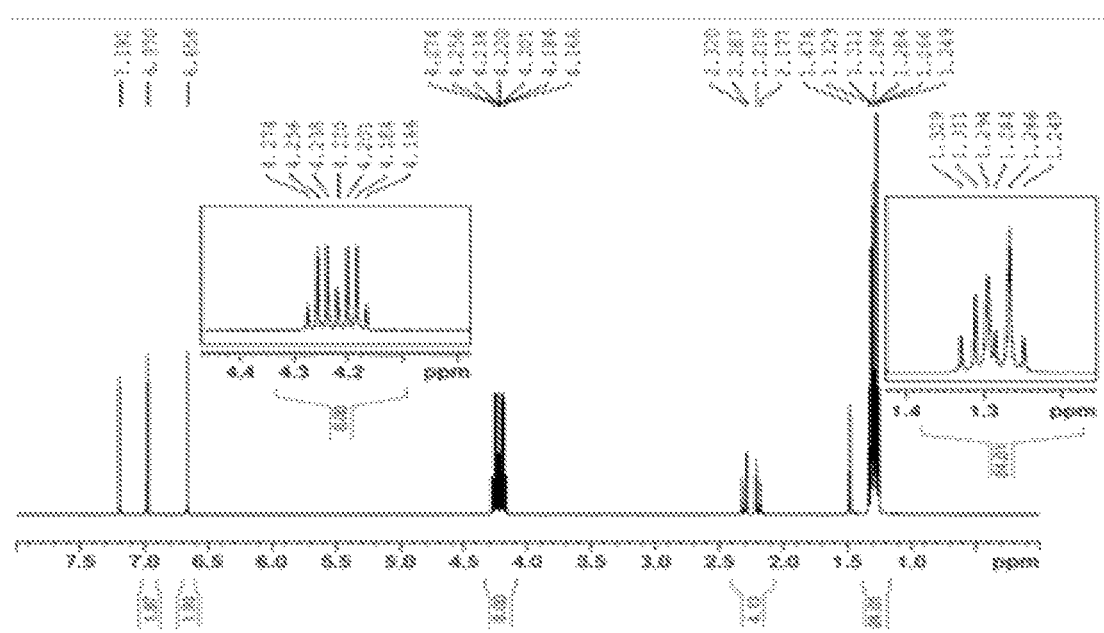
FIG. 1(b) illustrates $^1$H-NMR (Proton nuclear magnetic resonance) analysis of tetraethyl 3,3,3',3'-tetramethyl-2,2',3,3'-tetrahydro-1,1'-spirobiindane-5,5',6,6'-tetracarbonate.
Figure 1C:
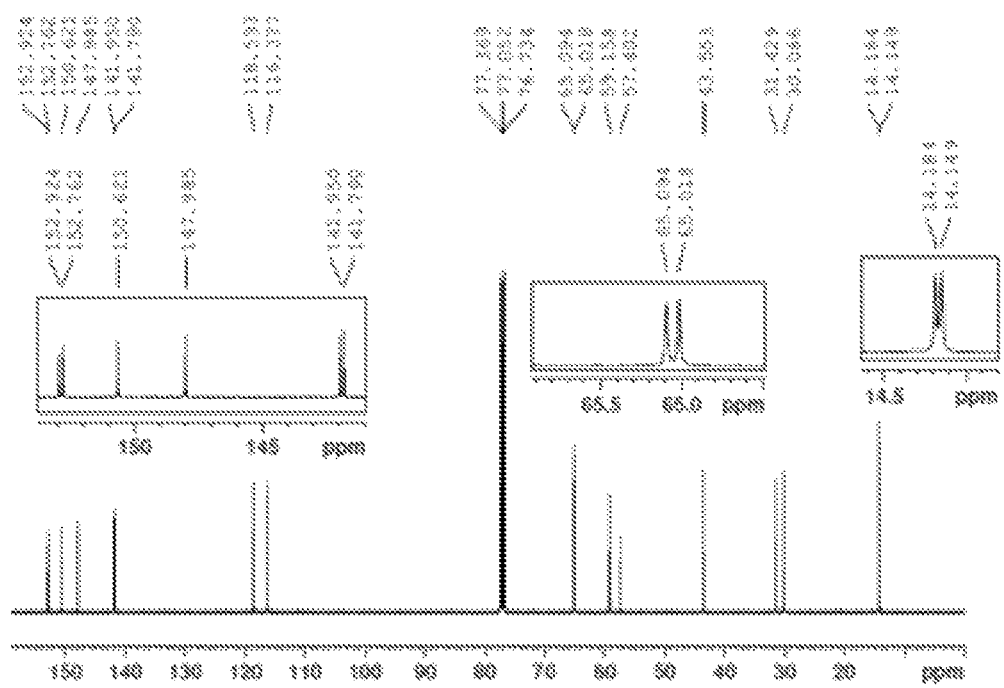
FIG. 1(c) illustrates $^{13}$C-NMR (Carbon nuclear magnetic resonance) analysis of tetraethyl 3,3,3',3'-tetramethyl-2,2',3,3'-tetrahydro-1,1'-spirobiindane-5,5',6,6'-tetracarbonate.

Tetraethyl 3,3,3',3'-tetramethyl-2,2',3,3'-tetrahydro-1,1'-spirobiindane-5,5',6,6'-tetracarbonate was further characterized by FTIR analysis, $^1$H NMR analysis and $^{13}$C NMR analysis, which is provided in FIG. 1(a), FIG. 1(b) and FIG. 1(c) respectively.

Experiment 2: Preparation of 3,3,3',3'-tetramethyl-2,2',3,3'-tetrahydro-1,1'-spirobiindane-5,5',6,6'-tetrayl tetrabenzoate Initially, the reactor was charged with 3,3,3',3'-tetramethyl-2,2',3,3'-tetrahydro-1,1'-spirobiindane-5,5',6,6'-tetraol (5 g), pyridine (9.4 mL) and anhydrous tetrahydrofuran (100 mL). Benzoyl chloride (8.4 mL) was then added to the reactor and the mixture was stirred at 100° C. was for 5 hours to obtain a resultant comprising 3,3,3',3'-tetramethyl-2,2',3,3'-tetrahydro-1,1'-spirobiindane-5,5',6,6'-tetrayl tetrabenzoate and the unreacted pyridine.

The reaction was monitored by thin layer chromatography. After completion of reaction, water and diethyl ether were added to the resultant to obtain a biphasic mixture comprising aqueous layer and an organic layer. The organic layer was separated from the biphasic mixture, followed by washing and drying under reduced pressure to obtain crude 3,3,3',3'-tetramethyl-2,2',3,3'-tetrahydro-1,1'-spirobiindane-5,5',6,6'-tetrayl tetrabenzoate.

Crude 3,3,3',3'-tetramethyl-2,2',3,3'-tetrahydro-1,1'-spirobiindane-5,5',6,6'-tetrayl tetrabenzoate was further purified by crystallization using a mixture of toluene and pet ether.

The purity of 3,3,3',3'-tetramethyl-2,2',3,3'-tetrahydro-1,1'-spirobiindane-5,5',6,6'-tetrayl tetrabenzoate was analyzed by HPLC and was found to be 96% and the yield was 80%.

The Melting point was 230° C.-233° C.

Figure 2A:
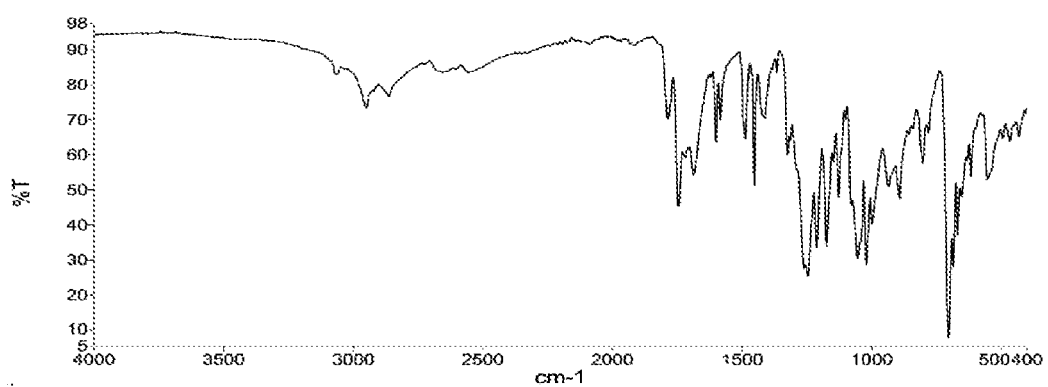
FIG. 2(a) illustrates FTIR (Fourier Transform Infrared) analysis of 3,3,3',3'-tetramethyl-2,2',3,3'-tetrahydro-1,1'-spirobiindane-5,5',6,6'-tetrayl tetrabenzoate.
Figure 2B:
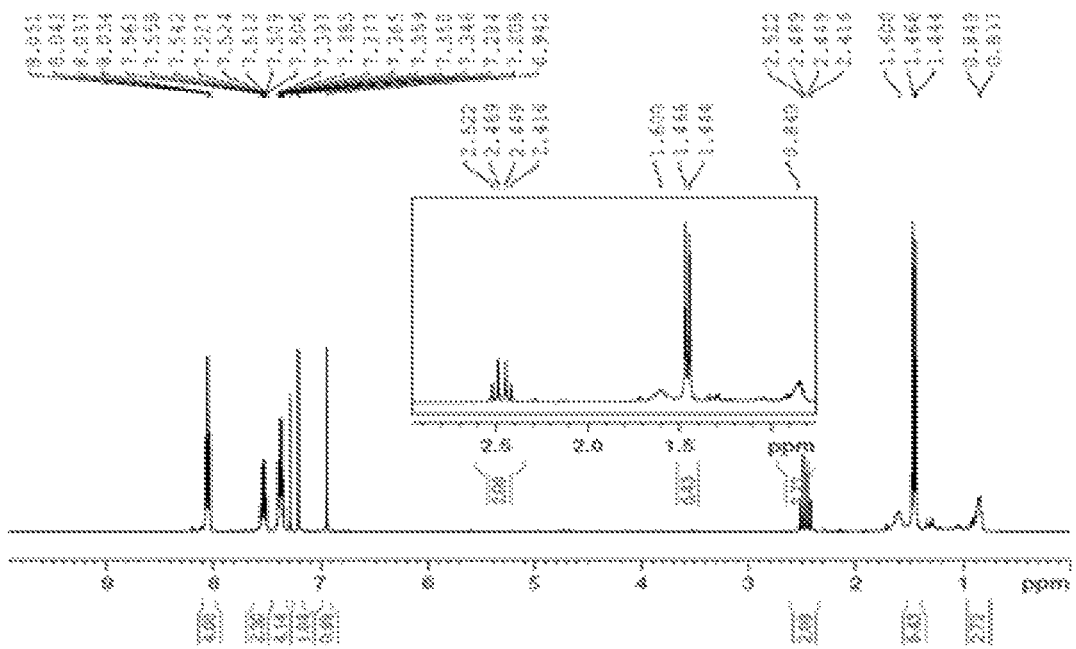
FIG. 2(b) illustrates $^1$H-NMR (Proton nuclear magnetic resonance) analysis of 3,3,3',3'-tetramethyl-2,2',3,3'-tetrahydro-1,1'-spirobiindane-5,5',6,6'-tetrayl tetrabenzoate.
Figure 2C:
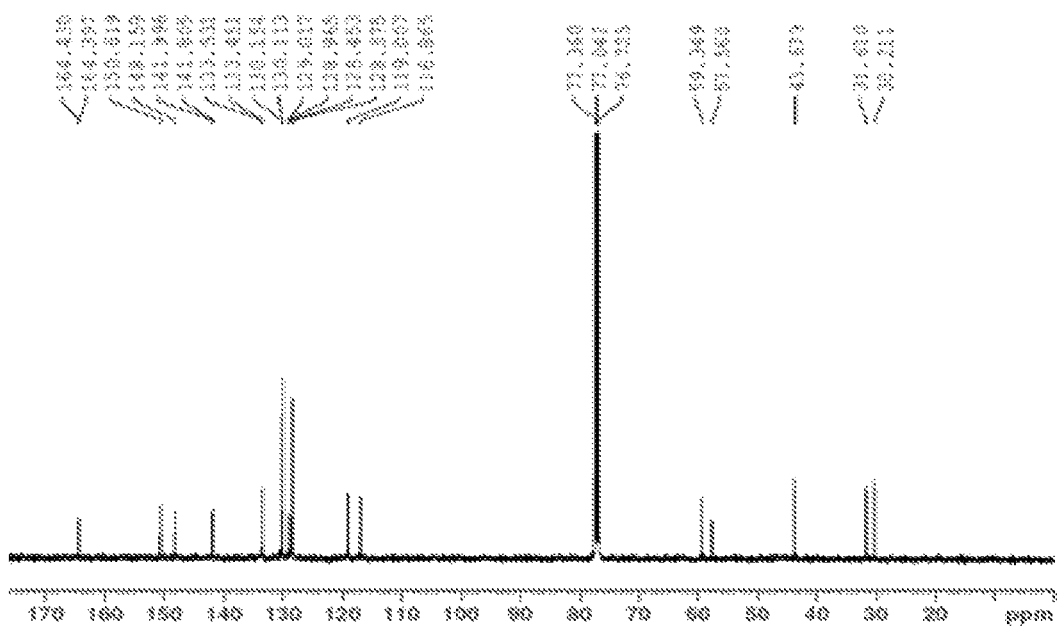
FIG. 2(c) illustrates $^{13}$C-NMR (Carbon nuclear magnetic resonance) analysis of 3,3,3',3'-tetramethyl-2,2',3,3'-tetrahydro-1,1'-spirobiindane-5,5',6,6'-tetrayl tetrabenzoate.

3,3,3',3'-tetramethyl-2,2',3,3'-tetrahydro-1,1'-spirobiindane-5,5',6,6'-tetrayl tetrabenzoate was further characterized by FTIR analysis, $^1$H NMR analysis and $^{13}$C NMR analysis, which is provided in FIG. 2(a), FIG. 2(b) and FIG. 2(c) respectively.

TECHNICAL ADVANCEMENTS

The present disclosure described herein above has several technical advantages including, but not limited to, the realization of spirobiindane derivatives of Formula I and the process for the preparation of the same, that is:

simple and economical process for the preparation of spirobiindane derivatives; and provides spirobiindane derivatives with high yield and high purity.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the invention to achieve one or more of the desired objects or results. While certain embodiments of the inventions have been described, these embodiments have been presented by way of example only, and are not intended to limit the scope of the inventions. Variations or modifications to the formulation of this invention, within the scope of the invention, may occur to those skilled in the art upon reviewing the disclosure herein. Such variations or modifications are well within the spirit of this invention.

The numerical values given for various physical parameters, dimensions and quantities are only approximate values and it is envisaged that the values higher than the numerical value assigned to the physical parameters, dimensions and quantities fall within the scope of the invention unless there is a statement in the specification to the contrary.

While considerable emphasis has been placed herein on the specific features of the preferred embodiment, it will be appreciated that many additional features can be added and that many changes can be made in the preferred embodiment without departing from the principles of the disclosure. These and other changes in the preferred embodiment of the disclosure will be apparent to those skilled in the art from the disclosure herein, whereby it is to be distinctly understood that the foregoing descriptive matter is to be interpreted merely as illustrative of the disclosure and not as a limitation.

The invention claimed is:

1. A process for preparation of a spirobiindane derivative of Formula I;

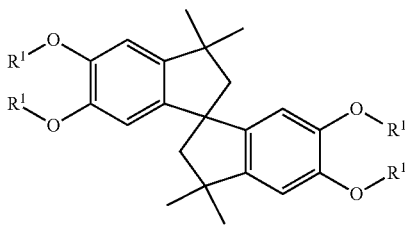

I wherein,
R$^1$ is selected from the group consisting of —COOC$_n$H$_{(2n+1)}$, where n=2, and —COPh,
wherein said process comprising
a. reacting 3,3,3',3'-tetramethyl-2,2',3,3'-tetrahydro-1,1'-spirobiindane-5,5',6,6'-tetraol, represented as Formula II

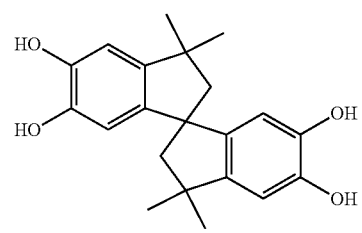

II with a protecting agent and pyridine as a base in a first fluid medium at a predetermined temperature for predetermined time period to obtain a resultant comprising a crude spirobiindane derivative and unreacted pyridine;
b. separating said unreacted pyridine from said resultant to obtain a crude spirobiindane derivative; and
c. crystallizing said crude spirobiindane derivative using at least one second fluid medium to obtain crystals of spirobiindane derivative of Formula I having purity greater than 95%;
wherein the mole ratio of said compound of Formula II and pyridine is in the range of 1:5 to 1:15.

2. The process as claimed in claim 1, wherein said protecting agent is selected from the group consisting of ethyl chloroformate and benzoyl chloride.

3. The process as claimed in claim 1, wherein the mole ratio of said compound of Formula II and said protecting agent is in the range of 1:4 to 1:10.

4. The process as claimed in claim 1, wherein said first fluid medium is at least one selected from the group consisting of tetrahydrofuran, dioxane, and toluene.

5. The process as claimed in claim 1, wherein said second fluid medium is at least one selected from the group consisting of toluene, hexane, pet ether, and diethyl ether.

6. The process as claimed in claim 1, wherein said predetermined temperature is in the range of 0° C. to 120° C.

7. The process as claimed in claim 1, wherein said predetermined time period is in the range of 2 hours to 6 hours.

* * * * *